United States Patent [19]
Klix et al.

[11] Patent Number: 5,998,669
[45] Date of Patent: Dec. 7, 1999

[54] PROCESS FOR PRODUCTION OF 2-AMINO-1,3-PROPANEDIOL

[75] Inventors: Russell C. Klix, Buffalo Grove; Deborah A. Davis, Waukegan; Owen J. Goodmonson, Buffalo Grove, all of Ill.

[73] Assignee: Abbott Laboratories, Abbott Park, Ill.

[21] Appl. No.: 09/154,848

[22] Filed: Sep. 17, 1998

[51] Int. Cl.$^6$ .................................................. C07C 209/26
[52] U.S. Cl. ............................................ 564/472; 564/473
[58] Field of Search ...................................... 564/472, 473

[56] References Cited

U.S. PATENT DOCUMENTS 5,023,379   6/1991   Felder et al. .

FOREIGN PATENT DOCUMENTS 9528379   10/1995   WIPO .

OTHER PUBLICATIONS

Felder, E., et al., "Process for amino alcohol manufacture", *Chemical Abstracts*, 107:120 (1987).

Iguchi, Y., "A process for the preparation of 2–amino–1, 3–propanediol", *Chemical Abstracts*.

*Primary Examiner*—Samuel Barts
*Attorney, Agent, or Firm*—Michael J. Ward

[57] ABSTRACT

The present invention relates to a process of making 2-amino-1,3-propanediol by reacting 1,3-dihyrdroxyacetone dimer with an amine compound.

15 Claims, No Drawings

PROCESS FOR PRODUCTION OF 2-AMINO-1,3-PROPANEDIOL

FIELD OF THE INVENTION

The present invention relates to a novel process for the production of 2-amino-1,3-propanediol.

BACKGROUND OF THE INVENTION

Amino alcohols are widely used intermediates in the manufacture of radiocontrast agents. 2-Amino-1,3-propanediol (serinol) is used in the production of Iopamidol. There are numerous synthetic routes for the preparation of amino alcohols, many of which have certain drawbacks when evaluated for manufacturing use. Some of the methods include reduction of amino acids or nitro alcohols. One of the simplest routes to 2-amino-1,3-propanediol involves the reductive amination of 1,3-dihydroxyacetone with ammonia. In this process, the solid dihydroxyacetone dimer is first dissolved in anhydrous liquid ammonia at low temperature to form an imine intermediate. Then a catalyst is added and the mixture is pressurized with hydrogen. Typically, the pressure may be as high as 1450 psi. Such high pressure is not desirable in an industrial setting from neither an operational nor from a safety point of view.

A process which would avoid the use of ammonia and high pressure would be advantageous in that it would be a safer process for the large scale production of 2-amino-1,3-propanediol.

SUMMARY OF THE INVENTION

The present invention relates to a process of making 2-amino-1,3-propanediol from 1,3-dihydroxyacetone dimer by reacting 1,3-dihydroxyacetone dimer with a substituted amine to form an alkoxyimine or imine, and reacting the alkoxyimine or imine with a reducing agent to form 2-amino-1.3-propanediol.

DETAILED DESCRIPTION OF THE INVENTION

The present invention provides a novel process for the preparation of 2-amino 1,3-propanediol, a key intermediate in the preparation of radiocontrast agents. The present invention provides a novel process for the preparation of 2-amino-1,3-propanediol by reacting an alkoxyamine or a benzylamine with 1,3-dihydroxyacetone dimer in the presence of a solvent to form intermediate, and reacting the intermediate with a reducing agent to form 2-amino-1,3-propanediol.

One embodiment of the present invention, as shown in Scheme 1, is making 2-amino-1,3-propanediol (3) by reacting 1,3-dihydroxyacetone dimer (1) with an alkoxyamine of the formula $NH_2OR_1$ to form an alkoxyimino derivative (2). The alkoxyimino may then be reacted with a reducing agent as described before to form 2-amino-1,3-propanediol (3).

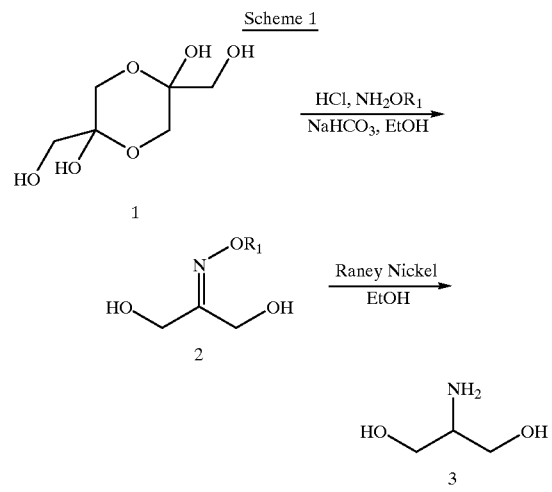

Preferred alkoxyamines for use in the present invention include, but are not intended to be limited to, methoxyamine, ethoxyamine, propoxyamine, and butoxyamine. Reducing agents suitable for the conversion of the imine (2) into 2-amino-1,3-propanediol (3) include, but is not intended to be limited to, Raney nickel and hydrogen. Other reducing agents may include palladium on carbon (1–30% by weight of catalyst on support) or platinum on carbon (1–10% by weight of catalyst on support).

Another embodiment of the present invention, as shown in Scheme 2, includes making 2-amino-1,3-propanediol (3) by first reacting an arylmethylamine of the general formula $NH_2CH_2R_2$, where $R_2$ is aryl, with 1,3-dihydroxyacetone dimer (1) to form the imine (4). For example, in Scheme 2, $R_2$ is phenyl ($C_6H_5$). The reaction may be carried out in aqueous methanol in the presence of an acid catalyst. Preferred acids include, but are not limited to, hydrochloric acid. The imine is hydrogenated to form 2-(N-(arylmethyl)) amino-1,3-propanediol (5) which then undergoes hydrogenolysis to form 2-amino-1,3-propanediol (3).

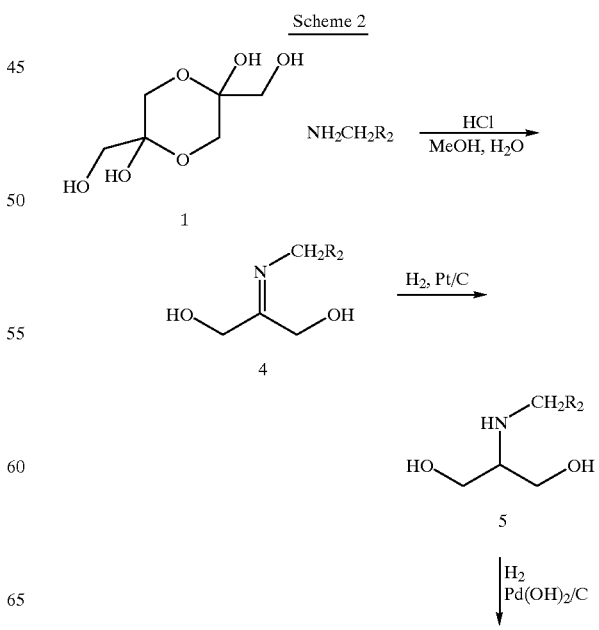

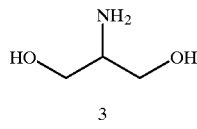

Hydrogenation of the imine may be performed by reacting the imine with hydrogen in the presence of a suitable catalyst. Suitable hydrogenation catalysts that can be used with the process of the present invention include, but is not intended to be limited to, platinum hydrogenation catalysts (1–10% on carbon, by weight of catalyst).

Hydrogenolysis of 2-(N-(arylmethyl))amino-1,3-propanediol (5) to form 2-amino-1,3-propanediol (3) may be done using a palladium catalyst with hydrogen. Preferably, the palladium hydrogenation catalyst is Pd(OH)$_2$/C or Pd/C. For example, debenzylation of 2-benzylamino-1,3-propanediol to form 2-amino-1,3-propanediol (3) may be done using 20% Pd(OH)$_2$/C.

The use of alkoxyamines and arylmethylamines with the novel process of the present invention allows the reaction to be carried out at low pressure and mild temperature. For example, the use of alkoxyamines and arylmethylamines with the novel process of the present invention allows the hydrogenation reaction to be carried out at a pressure from about 5 psi to about 100 psi. More preferably, the novel process of the present invention allows the hydrogenation reaction to be carried out at a pressure of about 40 psi. In addition, the use of alkoxyamines and arylmethylamines with the novel process of the present invention allows the reaction to be carried out at a temperature from about 5° C. to about 40° C. More preferably, the novel process of the present invention is carried out at a temperature from about 20° C. to about 25° C.

Alkoxyamines used include any amine of the general formula NH$_2$OR$_1$, in which R$_1$ is selected from the group consisting of alkyl, alkenyl, alkynyl, and aryl.

Arylmethylamines used include any amine of the general formula NH$_2$CH$_2$R$_2$, in which R$_2$ is aryl.

DEFINITIONS

"Alkyl" as used herein refers to straight or branched chain alkyls and substituted alkyls containing from 1 to 6 carbon atoms including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl; n-hexyl and the like.

The term "alkenyl" as used herein refers to a monovalent group derived from a hydrocarbon containing at least one carbon—carbon double bond by the removal of a single hydrogen atom. Alkenyl groups include, for example, vinyl (ethenyl), allyl (propenyl), butenyl, 1-methyl-2-buten-1-yl and the like.

The term "alkynyl" as used herein refers to a monovalent group derived from a hydrocarbon containing at least one carbon—carbon triple bond. Alkynyl groups include, for example, propynyl, butynyl, pentynl, 2-propynyl, 2-pentynyl, and the like.

The term "alkoxy" as used herein refers to R$_3$O—wherein R$_3$ is a alkyl group, as defined above. Examples of alkoxy include, but are not limited to, ethoxy, tert-butoxy, and the like.

The term "aryl" as used herein refers to a mono- or bicyclic carbocyclic ring system having one or more aromatic rings including, but not limited to, phenyl, naphthyl, tetrahydronaphthyl, naphthyridinyl, indanyl, indenyl and the like. Aryl groups can be unsubstituted or substituted with one or more substituents independently selected from alkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

Solvents suitable for the reactions may be optimized according to the starting materials used. For example, when alkoxyamines and arylmethylamines are reacted with 1,3-dihydroxyacetone dimer, the reaction may be carried out in a solvent. Suitable solvents include, but are not intended to be limited to, water and alcohols. Suitable alcohol solvents useful with the present invention include, but are not intended to be limited to, methanol, ethanol, propanol, isopropyl alcohol, butanol, and the like.

Acids suitable to form the arylmethylimine intermediate may include sulfuric, phosphoric, nitric, hydrochloric, and acetic acids. Preferably, the acid used in the reaction is hydrochloric acid.

Reducing agents suitable for use in the present invention include, but are not intended to be limited to, Raney nickel, platinum catalysts, and palladium catalysts with hydrogen. The palladium catalysts may be palladium/carbon, palladium hydroxide, palladium (black), and palladium supported.

The platinum hydrogenation catalyst may be from about 3% to about 100% by weight of the entire catalyst deposited on a carbon support. Preferably, the platinum hydrogenation catalyst is 5% by weight of the entire catalyst deposited on a carbon support.

Hydrogenolysis of 2-(N-(arylmethyl))amino-1,3-propanediol may be performed using a palladium hydrogenation catalyst from about 3% to about 100% weight of the entire catalyst deposited on a carbon support. Preferably, the palladium hydrogenation catalyst is 20% Pd(OH)$_2$ by weight of the entire catalyst deposited on a carbon support.

EXAMPLE 1

A suspension of dihydroxyacetone dimer (27.0 grams (g), 0.15 moles (mol) in 95% ethanol (150 milliliters (mL)) was prepared and methoxyamine hydrochloride (25.0 g, 0.30 mol) and sodium bicarbonate (25.2 g, 0.30 mol) were added to the suspension. The reaction mixture was stirred at room temperature overnight and then filtered. The filtrate was concentrated to afford 34.2 g (96%) of 2-methoxyimino-1,3-propanediol as an oil. A 2-methoxyimino-1,3-propanediol solution was prepared by adding 2-methoxyimino-1,3-propanediol (5.0 g, 42 millimoles (mmol)) in 50 mL of dry ethanol and adding 5.0 g of Raney nickel (the Raney nickel was washed with ethanol prior to use). The reaction vessel was pressurized with 40 psi H$_2$. After 4 hours of agitation, the vessel was vented and purged with nitrogen, and the contents were filtered through a fiberglass pad which was washed with ethanol. The solution was cooled and then acidified with 7 mL of 6.3 Molar (M) HCl/ethanol. The solution was concentrated and the resulting gum was triturated with acetonitrile and ethanol to afford 1.9 g of 2-amino-1,3-propanediol hydrochloride. An additional 1.2 g of 2-amino-1,3-propanediol hydrochloride was obtained from the filtrate affording a total yield of 71%.

EXAMPLE 2

Concentrated aqueous HCl (98.65 g, 1.00 mol) and benzylamine (107.16 g, 1.00 mol) were added to a suspension of dihydroxyacetone dimer (90.08 g, 0.50 mol) in methanol (MeOH) (900 mL) and water (180 mL). The solids dissolved with occasional swirling over 15 minutes. To the colorless solution was added 5% Pt/C (9.0 g) and the reaction vessel was pressurized with 40 psi $H_2$. After 19 hours of agitation, the vessel was vented and purged with nitrogen, and then the contents were filtered through a fiberglass pad which was washed with methanol (100 mL). The solution was concentrated to approximately 200 mL on a rotary evaporator and then dissolved in methanol-$H_2O$ (4:1, 1200 mL). To the solution was added 20% $Pd(OH)_2/C$ (9 g) and the reaction vessel was pressurized with 40 psi $H_2$. After 18 hours of agitation, the vessel was vented, purged with nitrogen and the contents were filtered through a fiberglass pad that was washed with methanol. The solution was concentrated to an amber oil which was evaporated twice with toluene (2×200 mL) to remove residual water. This treatment left behind a sticky off-white solid that was recrystallized from methanol (50 mL) to yield after drying (50°, 3 mm Hg, 18 hours), 95.74 g of 2-amino-1,3-propanediol hydrochloride as a white crystalline solid (75% yield): mp 106–108° C.; $^1H$ NMR (300 MHz, DMSO-d6) 8.10 (s, 3H), 5.15 (s, 2H), 3.55 (m, 4H), 3.05 (quint., 1H); $^{13}C$ NMR (75 MHz, DMSO-d6) 58.7, 54.6; anal. calcd. for $C_3H_{10}ClNO_2$ C, 28.25; H, 7.90; N, 10.98; found C, 28.51; H, 7.89; N, 10.86.

What is claimed is:

1. A process of making 2-amino-1,3-propanediol comprising:
   (a) reacting 1,3-dihydroxyacetone dimer with an amine of the formula, $NH_2OR_1$, wherein $R_1$ is selected from the group consisting of alkyl, alkenyl, alkynyl, or aryl, in the presence of a solvent to form an intermediate alkoxyimine; and
   (b) reacting the intermediate with a reducing agent to form 2-amino-1,3-propanediol.

2. A process of claim 1 wherein said reducing agent comprises hydrogen and Raney Nickel as a catalyst.

3. A process of claim 1 wherein the said reducing agent comprises a palladium catalyst and hydrogen.

4. A process of claim 3 wherein the said reducing agent comprises a palladium catalyst is about 5% palladium by weight of the entire catalyst deposited on a carbon support.

5. A process of claim 1 wherein step (b) is carried out at a pressure in the range from about 5 psig to about 100 psig.

6. A process of claim 1 wherein step (b) is carried out at a temperature of 5° C. to 200° C.

7. A process of making 2-amino-1,3-propanediol comprising:
   (a) reacting 1,3-dihydroxyacetone dimer with an amine of the formula, $NH_2CH_2R_2$, wherein $R_2$ is aryl, in the presence of a solvent to form an intermediate imine; and
   (b) reacting the intermediate with a reducing agent to form 2-amino-1,3-propanediol.

8. A process of claim 7 wherein said arylmethylimine is hydrogenated to form 2-(N-(arylmethyl))amino- 1,3-propanediol.

9. A process of claim 8 wherein said 2-(N-(arylmethyl))amino-1,3-propanediol is subjected to hydrogenolysis to form 2-amino-1,3-propanediol.

10. A process of claim 8 wherein said hydrogenation reaction is carried out using a platinum catalyst and hydrogen.

11. A process of claim 9 wherein said hydrogenolysis reaction is carried out using a palladium catalyst and hydrogen.

12. A process of claim 10 wherein said platinum hydrogenation catalyst is about 5% platinum by weight of the entire catalyst deposited on a carbon support.

13. A process of claim 11 wherein said palladium catalyst is 20% palladium hydroxide by weight of the entire catalyst deposited on a carbon support.

14. A process of claim 7 wherein step (b) is carried out at a pressure in the range from about 5 psig to about 100 psig.

15. A process of claim 7 wherein step (b) is carried out at a temperature of 5° C. to 200° C.

* * * * *